United States Patent
Kossak et al.

(10) Patent No.: US 7,082,950 B2
(45) Date of Patent: Aug. 1, 2006

(54) MANUALLY HELD DENTAL FLOSSERS

(75) Inventors: Michael Kossak, Chevy Chase, MD (US); Dalita Tomellini, Rehoboth, MA (US); Paul Kotowski, Foster, RI (US)

(73) Assignee: Michael Kossak, Chevy Chase, MD (US)

( * ) Notice: Subject to any disclaimer, the term of this patent is extended or adjusted under 35 U.S.C. 154(b) by 794 days.

(21) Appl. No.: 09/975,558

(22) Filed: Oct. 12, 2001

(65) Prior Publication Data

US 2002/0078974 A1 Jun. 27, 2002

Related U.S. Application Data

(63) Continuation-in-part of application No. 09/689,626, filed on Oct. 13, 2000, now abandoned.

(51) Int. Cl.
*A61C 15/00* (2006.01)
(52) U.S. Cl. ..................... 132/325; 132/326
(58) Field of Classification Search ........ 132/323–329, 132/322
See application file for complete search history.

(56) References Cited

U.S. PATENT DOCUMENTS

| | | |
|---|---|---|
| 1,700,550 A | 1/1929 | Stafford |
| 3,106,216 A | 10/1963 | Kirby |
| 3,340,881 A | 9/1967 | Cowan |
| 3,472,247 A | 10/1969 | Borsum et al. |
| 3,534,745 A | 10/1970 | Waters |
| 3,667,483 A | 6/1972 | McCabe |
| 3,734,107 A | 5/1973 | Thierman |
| 3,746,017 A | 7/1973 | Casselman |
| 3,759,274 A | 9/1973 | Warner |

(Continued)

FOREIGN PATENT DOCUMENTS

CA 1000533 11/1976

(Continued)

*Primary Examiner*—John J. Wilson
*Assistant Examiner*—Robyn Doan
(74) *Attorney, Agent, or Firm*—Lowe Hauptman Berner, LLP

(57) ABSTRACT

A dental flossing device is characterized by a flossing circuit comprised of a flossing supply spool and a take-up spool mounted to a housing. The floss feeds from the supply spool along a pair of prongs forming a fork extension of the handle and is stretched across the prongs and appropriately tensioned to be inserted into a users mouth for flossing. To maintain tension, a pair of ratchet pawls are jointly engageable with a ratchet mounted for co-rotation with the take-up spool. The pawls are offset relative to the ratchet teeth to ensure appropriate tension. Tension on the supply spool side of the flosser is achieved with a tension arm in constant engagement with tension teeth co-rotatably mounted with the spool. When a floss advancing trigger is not depressed, a brake pawl formed at one end of the trigger is spring biased into locking engagement with these teeth while the tension arm assures proper tension on the supply side. In an alternative preferred embodiment, only one tensioning ratchet pawl engages the ratchet mounted for co-rotation with the take-up spool. A different ratchet pawl, mounted to one end of a ratchet arm pivotally secured to the flosser housing beneath the ratchet, is engaged by the trigger to drivingly contact the ratchet to rotate the take-up spool. In this latter embodiment, the brake pawl is replaced with a projection formed on the trigger that is adapted to engage the supply spool tensioning ratchet to lock the ratchet in the released position of the trigger to prevent supply spool rotation and maintain the floss circuit in a tight condition.

18 Claims, 8 Drawing Sheets

U.S. PATENT DOCUMENTS

| | | |
|---|---|---|
| 3,908,677 A | 9/1975 | Beach |
| 3,927,687 A | 12/1975 | Thierman |
| 4,031,908 A | 6/1977 | Ting |
| D251,859 S | 5/1979 | Kent |
| 4,235,253 A | 11/1980 | Moore |
| 4,245,658 A | 1/1981 | Lecourturier |
| 4,319,595 A | 3/1982 | Ulrich |
| 4,326,549 A | 4/1982 | Hinding |
| 4,458,702 A | 7/1984 | Grollimund |
| 4,518,000 A | 5/1985 | Leverette |
| 4,586,521 A | 5/1986 | Urso |
| 4,605,025 A | 8/1986 | McSpadden |
| 4,706,695 A | 11/1987 | Urso |
| 4,756,202 A | 7/1988 | Kawamoto |
| 4,830,032 A | 5/1989 | Jousson |
| 4,883,080 A | 11/1989 | Lang |
| 5,016,660 A | 5/1991 | Boggs |
| 5,033,150 A | 7/1991 | Gross et al. |
| 5,038,806 A | 8/1991 | Ewald |
| 5,085,236 A | 2/1992 | Odneal et al. |
| 5,094,256 A | 3/1992 | Barth |
| 5,176,157 A | 1/1993 | Mazza |
| 5,183,064 A | 2/1993 | Barth |
| 5,183,065 A | 2/1993 | Mason |
| 5,184,632 A | 2/1993 | Gross et al. |
| 5,186,191 A | 2/1993 | Loubier |
| 5,188,133 A | 2/1993 | Romanus |
| 5,207,773 A | 5/1993 | Henderson |
| 5,224,500 A | 7/1993 | Stella |
| 5,269,331 A | 12/1993 | Tanriverdi |
| 5,678,578 A * | 10/1997 | Kossak et al. ............... 132/322 |
| 5,822,874 A | 10/1998 | Nemes |
| 6,095,192 A | 8/2000 | Gleasman et al. |

FOREIGN PATENT DOCUMENTS

| | | |
|---|---|---|
| DE | 3625991 | 1/1988 |
| EP | WO 90/11057 | 10/1990 |
| EP | 0 453418 | 10/1991 |
| GB | 2141935 | 1/1985 |
| TW | 139048 | 4/1980 |
| TW | 52610 | 12/1982 |
| TW | 098442 | 5/1986 |

* cited by examiner

FIG. 8C
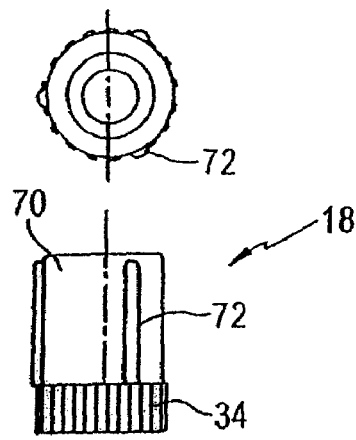
FIG. 8B
FIG. 8A
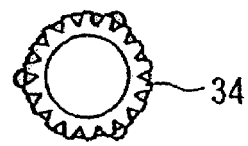
FIG. 9B
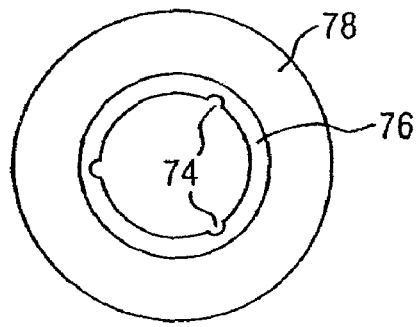
FIG. 9A
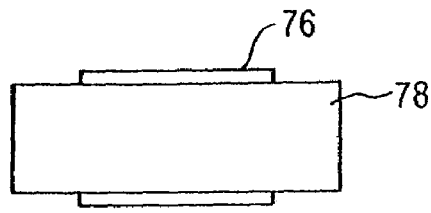

MANUALLY HELD DENTAL FLOSSERS

RELATED APPLICATIONS

This application is directed to inventions that are improvements over flossing equipment disclosed in U.S. Pat. No. 5,678,578, to Kossak et. al. This application is a continuation-in-part of U.S. application Ser. No. 09/689,626 filed Oct. 13, 2000 now abandoned.

TECHNICAL FIELD

The present invention relates generally to tooth flossing and, more particularly, to manual floss holders for use in the avoidance in periodontal diseases.

BACKGROUND ART

Flossing is the only effective method for cleaning between teeth to remove plaque buildup which is the primary causative agent of gingivitis, periodontitis, and tooth decay. The most commonly used method of flossing is to strip a large piece of floss off a dispenser, about one and one half to two feet, wrap it around one's fingers, and to then work an exposed piece of floss between the fingers of both hands up and down against the tooth surfaces defining the interproximal spaces between the teeth. Ideally, a freshly exposed piece of floss is used for each interproximal space. Otherwise, continued use of the same exposed piece will likely result in transference of plaque and bacteria from one interproximal space to another.

For optimal results, the foregoing flossing procedure should be performed daily. However, only the most conscientious individuals adhere to such a strict schedule. This is because flossing is generally regarded as an unpleasant experience since there are a number of problems which occur during flossing which result in a failure to floss daily. One such problem, for example, is that it can be difficult and painful for the individual to wrap the floss tightly enough around the fingers to maintain the needed tension, and then to unwrap and rewrap the used piece to expose a fresh piece to floss the next interproximal space. It is also unpleasant to handle the wet, odorous, used floss and to wrap such material about the fingers of the hands. Additionally, gagging may occur during flossing and it can be painful to hold one's mouth open long enough and wide enough to floss every tooth, particularly rearwardly located teeth. Furthermore, it is often difficult to work with fingers from both hands in the mouth and the force applied to get the floss between the teeth can be excessive. Often, the floss snaps into the gum causing it to bleed. Furthermore, although floss is relatively inexpensive, quite a bit is used in a single cleaning and there is considerable waste, considering that the end portions of the floss are not used for cleaning but merely to be wrapped around each hand to provide the necessary anchoring for proper tension.

A number of dental flossing devices have been proposed for commercialization or are commercially available for the purpose of avoiding the use of one's fingers to position the floss correctly. For various reasons, most of these devices, if not all, are not widely accepted or practical and have not resulted in the increased regularity of flossing among the general population.

One problem associated with the manual flossers of which I am aware is the inability of the flossers to impart sufficient tension to the exposed piece of floss during the flossing operation. To be of practical use, a mechanical flosser must have a flossing circuit whereby a high degree of tension is maintained against the exposed piece of floss during use, such tension being sufficient to enable the exposed floss to be threaded through a tight contact into each interproximal space. Numerous prior art flossers of which I am aware utilize a take-up spool for receiving used floss and a supply spool for supplying fresh floss into a part of the flossing circuit which is exposed for placement in the individual's mouth. Not only do these flossers fail to provide sufficient tension, most if not all rely upon structures wherein the take-up spool is located within a housing. This is extremely unhygienic, contaminates the flosser both inside and out, and creates an odorous situation.

Other problems associated with flossers of which I am aware is that the mechanism tend to be complicated. If the floss in the circuit breaks, as normally occurs each time an individual flosses, it is virtually impossible for the flosser to rethread the floss onto the take-up spool.

Still other flossers of which I am aware rely upon a jet of water. However, the use of a water jet has been classically shown to be ineffective as a flossing substitute and only works on the outsides of the teeth and not interproximally, which is the area most vulnerable to decay and periodontal disease or bone loss.

It is accordingly one object of the present invention to provide a dental flossing device which is easy to use and easy to rethread in the event of floss breakage.

Another object is to locate a take-up supply spool for spent floss in an external position on the device to improve hygiene.

Still another object is to provide a manually operated flossing device which is both easy to use and capable of maintaining a high degree of tension to enable proper flossing usage.

DISCLOSURE OF THE INVENTION

The present invention is directed to a flossing device to facilitate the insertion of floss between teeth. The device comprises a housing including a fork extension extending from the housing and a pair of prongs with grooves for guiding the floss in a circuit which spans a space between the prongs. A floss supply spool is rotatably mounted to the housing and a floss take-up spool is also rotatably mounted to the housing. An actuating mechanism for rotating the take-up spool is provided to advance the floss within the floss circuit. The invention features a first tensioning mechanism connected to the floss take-up spool to tension the floss when the actuating mechanism is deactivated. The tensioning mechanism includes at least one pawl simultaneously engageable with a ratchet co-rotatably mounted to the take-up spool. A second tensioning mechanism is connected to the supply spool to cooperate with the first tensioning mechanism to tension the floss during periods when the actuating mechanism is deactivated. This second tensioning mechanism is preferably a tension arm having a distal end in contact with one of a plurality of teeth formed along the periphery of a mounting post to which the supply spool is co-rotatably mounted.

In one embodiment, two separate pawls are used to form the first tensioning mechanism that engage ratchet teeth co-rotatably mounted with the take-up spool in a offset manner to each other to ensure that tension is always imparted to the take-up spool.

The actuating mechanism is preferably a trigger that is spring biased to project outwardly from the flossing device housing. One end of the trigger is formed with an actuating pawl that is adapted to engage and partially rotate a drive ratchet co-rotatably mounted to the take-up spool when the trigger is depressed. A second ratchet co-rotatable with the first ratchet functions as part of the first tensioning mechanism as a result of its constant engagement with the two tensioning pawls.

The first and second ratchets are preferably integrally molded together. The take-up spool includes a downwardly projecting shaft adapted to be fixedly attached to the first and second ratchets for co-rotation therewith.

In a preferred embodiment, the tension arm of the second tensioning element is in constant engagement between two of the supply spool mounting post ratchet teeth to lockingly engage the mounting post and prevent supply spool rotation when the trigger is not being depressed to advance floss. To maintain supply spool lock-up during trigger deactivation, a portion of the trigger within the housing and opposite the depressed trigger end is adapted to pivot into abutting contact with the distal end of the tension arm to thereby prevent supply spool mounting post rotation in the unwinding direction.

Still with reference to the preferred embodiment, the trigger actuating mechanism is neither directly spring biased nor integrally formed with an actuating pawl at one end thereof as is the case in the first above described embodiment. Instead, a ratchet arm is pivotally secured at one end thereof within the housing and the opposite end extends towards a position immediately adjacent the trigger. This opposite end of the ratchet arm adjacent the trigger is resiliently biased towards the trigger. An actuating pawl is formed to project upwardly from this ratchet bar opposite end so that trigger depressment is operable to pivot the pawl carried on the ratchet bar opposite end, as well as the ratchet bars, into driving engagement with a single take-up spool ratchet. With this construction, less force is necessary to depress the trigger as a result of reduced spring force and the advantageous location of the pawl at the distal end of the ratchet arm so as to obtain an improved leveraging effect.

The supply spool in the above embodiments is preferably formed with ribs at spaced intervals along an inner cylindrical surface thereof. These ribs are adapted to engage corresponding keyways in axial sliding engagement formed in an upper portion of a supply spool mounting post. This supply spool mounting post is attached to a cylindrical boss projecting upwardly from the bottom of the floss housing for rotation thereabout. A bottom of the post is formed with the tensioning teeth.

The above and still further objects features and advantages of the present invention will become apparent upon consideration of the following detailed description of a specific embodiment thereof, especially when taken in conjunction with accompanying drawings.

BRIEF DESCRIPTION OF THE DRAWING

FIGS. 8A, 8B and 8C are respective bottom, side and top plan views of a supply spool mounting post;

FIGS. 9A and 9B are respective side and top plan views of a unique floss supply spool according to the present invention;

BEST MODE FOR CARRYING OUT THE INVENTION

Figure 1:
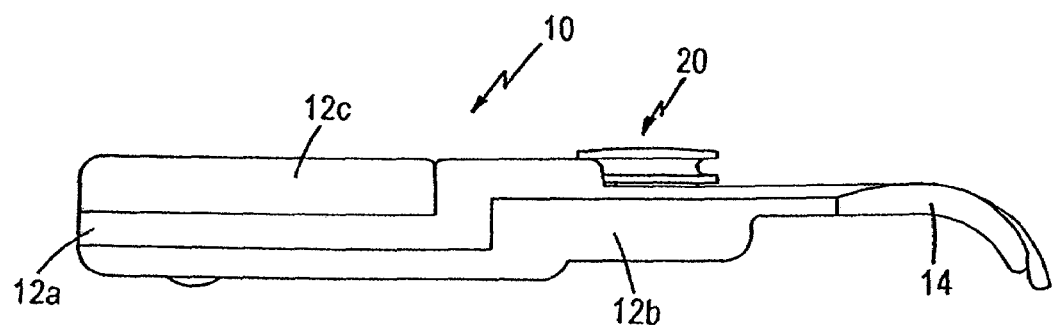
FIG. 1 is a side view of the cover and housings of the dental flosser according to one embodiment of the present invention.
Figure 2:
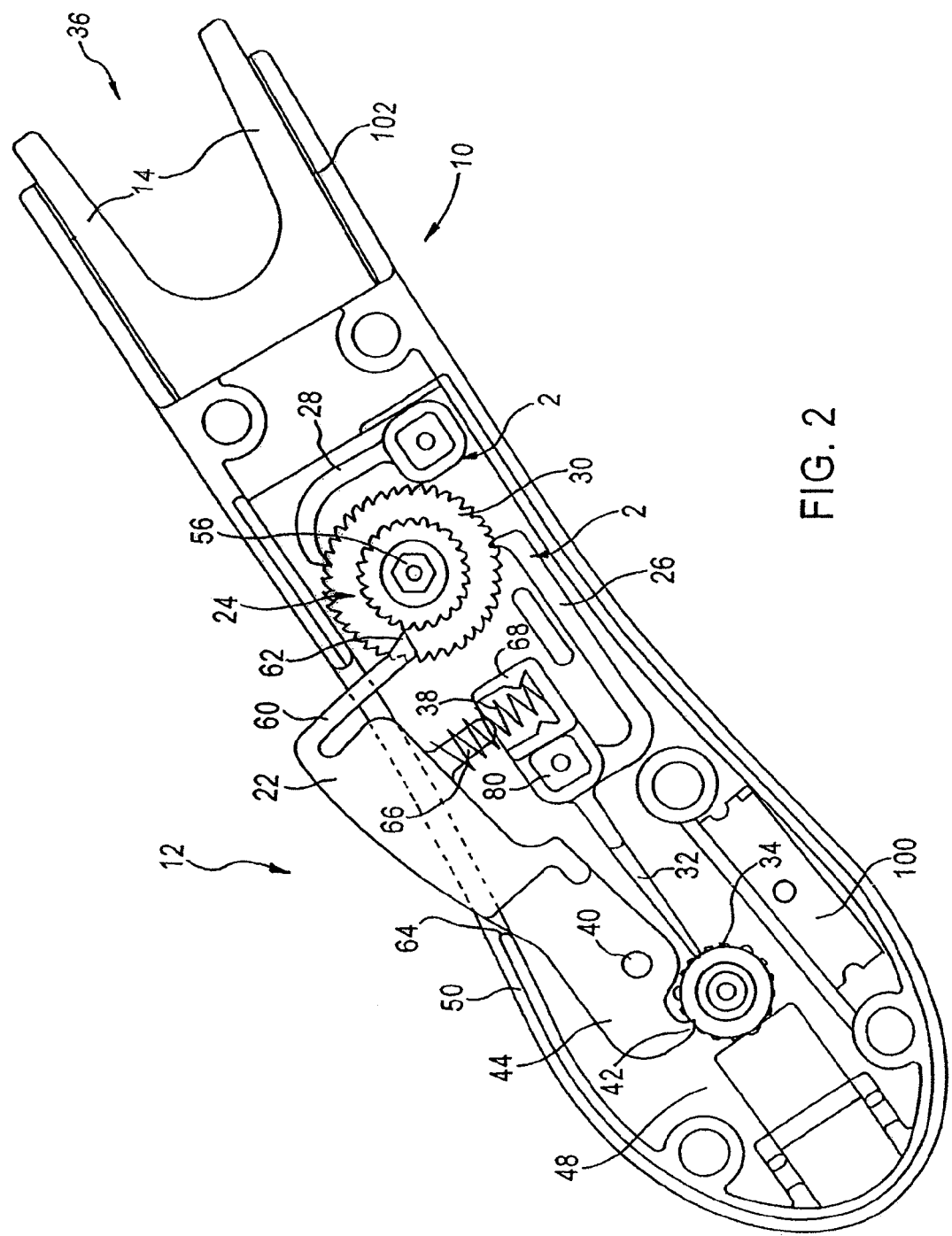
FIG. 2 is an enlarged top plan view with the cover and top housing removed, of the drive and tensioning mechanisms in the flosser of FIG. 1.
Figure 3:
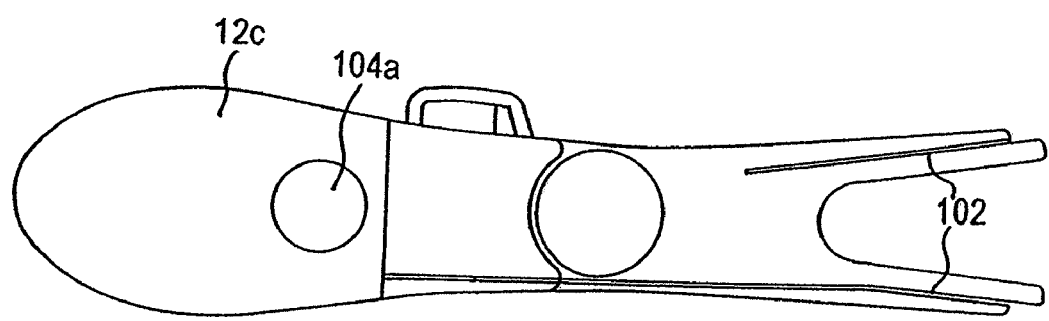
FIG. 3 is a top plan view of the flosser of FIG. 2 in fully assembled condition.

Referring to FIGS. 1 and 2, there is disclosed a manual dental flosser 10 having a handle or body portion 12 formed from a top housing 12a and a bottom housing 12b from which bottom housing a pair of fork arms 14 project forwardly in laterally spaced relationship to each other. The handle 12 supports a floss supply spool 16 normally covered with a snap-on cover 12c. Supply spool 16 is uniquely mounted to a supply spool mounting post 18, and a take-up spool 20 is mounted forwardly (i.e. closer to the fork arms 14) of the floss supply spool in the novel manner described below. Manually depressing a trigger 22 projecting from a side of handle 12 is operable to partially rotate an input drive ratchet 24, co-rotatably mounted to the take-up spool 20, which in turn co-rotates the take-up spool in a counter clockwise direction. The take-up spool 20 is rotatable in one direction only, i.e. to wind used floss, and is preferably located advantageously above top housing 12a. Undesired rotation of take-up spool 20 in the clockwise direction is prevented by means of two pawls 26 and 28 engaging a large diameter ratchet 30 located beneath, and in coaxial alignment with, the input drive ratchet 24. As this counter clockwise winding action occurs during depressing of trigger 22, the floss supply spool 16, also located atop housing 12a, is simultaneously rotated counter clockwise in an unwinding direction as a result of the pulling action of floss being wound onto the floss take-up spool 20. A tension arm 32 in constant engagement with brake or tension teeth 34 formed on the supply spool mounting post 18 in the unique manner described below imparts a constant degree of tension against the supply spool 16 to prevent excessive unwinding action. In this manner, fresh floss is progressively advanced in a flossing circuit where it is stretched and tensioned across a space 36 formed between the pair identical prongs or forks 14 which define a forwardly extending portion of the bottom housing 12a.

Release of the trigger mechanism 22 causes the trigger to be pushed by a return spring 38 to its outermost position shown in FIG. 2 about a pivot post 40. This movement causes a brake tooth 42 formed on a rearwardly extending portion 44 of the trigger 22 to engage teeth 34 when the trigger is released. This braking action, coupled with the interaction of tensioning pawls 26 and 28 against ratchet teeth 30, advantageously imparts a high degree of tension to the floss in the flossing circuit. In accordance with a unique feature of this invention high tension is assured by designing ratchet pawls 26 and 28 in an offset manner to ensure that taut tension is being maintained.

Figure 6:
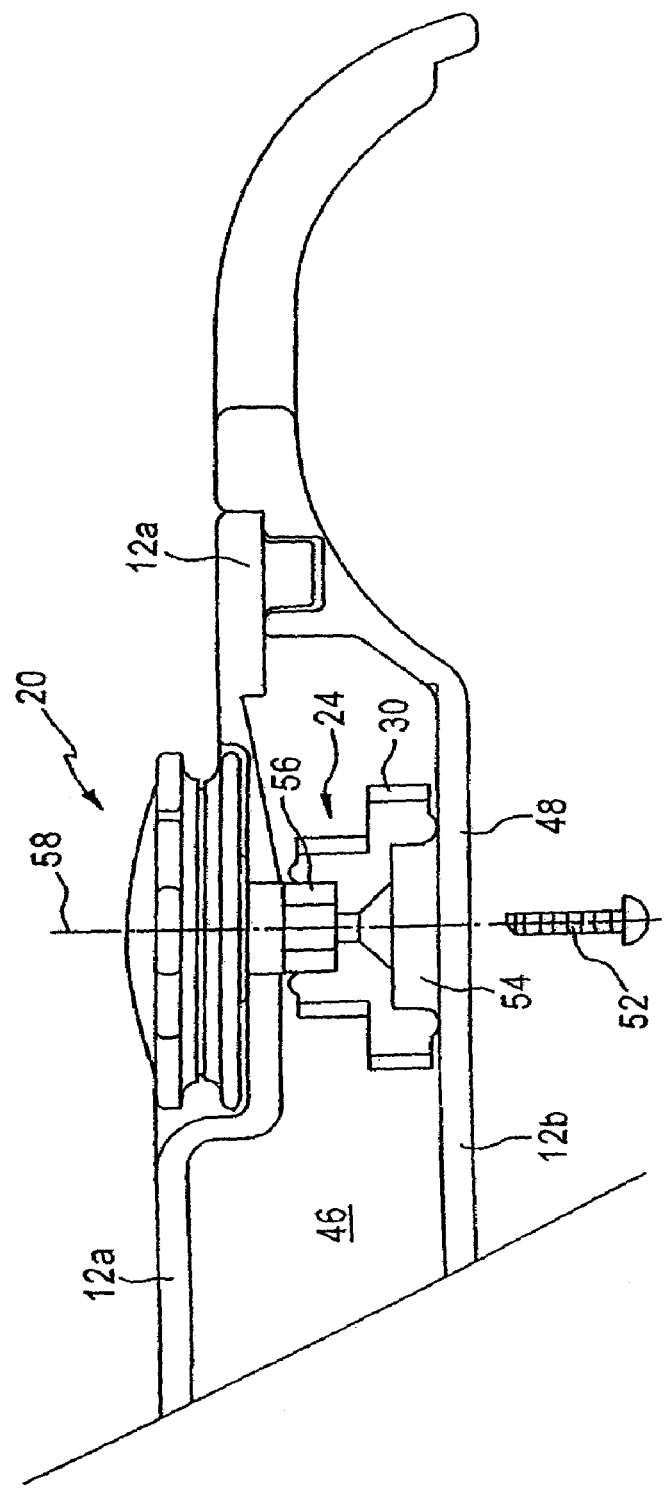
FIG. 6 is an enlarged sectional view of one embodiment of the take-up spool and underlying drive and tensioning ratchet mechanisms.

More specifically, the bottom housing 12b in the preferred embodiment is formed with an upward facing cavity 46 defined by a bottom wall 48 and upwardly projecting sides 50. The take-up spool drive and tensioning ratchet mechanisms 24, 30, preferably molded of plastic to be of integral or unitary construction, is mounted in a forward portion of cavity 50 with a screw 52 received in the underside of bottom wall 48 (see FIG. 6). More specifically, a bottom surface of the lower large diameter ratchet 30 may be fitted to a mounting post 54 projecting upward from cavity bottom wall 48. Screw 52 extends upwardly through mounting post 54 for threaded contact with a downwardly projecting mounting stub-shaft 56 projecting downwardly from take-up spool 20. The outer surface of this shaft 56 may have a hexagonal configuration as best depicted in FIG. 6 so that the take-up spool 20 co-rotates with ratchets 24, 30 about the rotational axis 58 defined by screw 52.

It is also within the scope of this invention to have screw 52 threadedly engaged only the ratchet mechanism 24, 30 without threaded contact with the stub shaft 56. With this modification, it will be appreciated that take-up spool 20 may be easily removed from the flosser 10 for cleaning by simply pulling up on the take-up spool so that the hexagonal shape of stub shaft 56 can slide upwardly and release from the corresponding central opening in ratchet 24 as a result of smooth sliding withdrawal and insertion contact.

Trigger 22 is a thin flat member formed with a pawl arm 60 projecting inwardly from the trigger at a forwardmost portion thereof as best depicted FIG. 2. Pawl arm 60 includes a pawl 62 at an innermost distal end thereof that is in co-elevational alignment with the teeth of input drive ratchet 24. Trigger 22 normally projects outwardly from side housing wall 50 through a cutout 64 against the bias of compression spring 38 which is mounted to trigger 22 on a mounting post 66 extending inwardly from the trigger. The inner end of the laterally extending spring 38 is received in a square mounting post 68 (projecting upwardly from housing bottom wall 48) which opens laterally outward towards the trigger. Trigger 22 is maintained in its laterally outermost or rest position by the compression spring 38 so that the trigger actuated pawl 62 is normally out of contact with the drive ratchet 24.

The floss supply spool mounting post 18 as best depicted in FIGS. 8A–8C, is shown to include an upper spool mounting portion 70 extending for a major portion of the post height. It is also within the scope of this invention to have screw 52 threadedly engaged only the ratchet mechanism 24, 30 without threaded contact with the sub-shaft 56. With this modification, it will be appreciated that take-up spool 20 may be easily removed from the flosser 10 for cleaning by simply pulling up on the take-up spool so that the hexagonal shape of sub-shaft 56 can slide upwardly and release from the corresponding central opening in ratchet 24 as a result of smooth sliding withdrawal and insertion contact. Circumferentially spaced ribs 72 formed on mounting portion 70 which are adapted to engage with corresponding keyways 74 (FIGS. 9A and 9B) formed on the inner-cylindrical surface of supply spool hub 76 on which floss 78 is wound. With this advantageous configuration, the preferably plastic supply spool hub or core 76 is placed over the top of the post 18 for removal or replacement such that the keyways 74 engage the ribs 72 to thereby prevent the spool from rotating on the post 70, allowing for co-rotation therebetween. The bottom portion of post 70 is formed with the circumferentially spaced teeth 34 which are in co-elevational alignment with the tension arm 32 projecting rearwardly from a mounting projection 80 extending upwardly from the housing bottom wall 48 (see FIG. 2).

Figure 5:
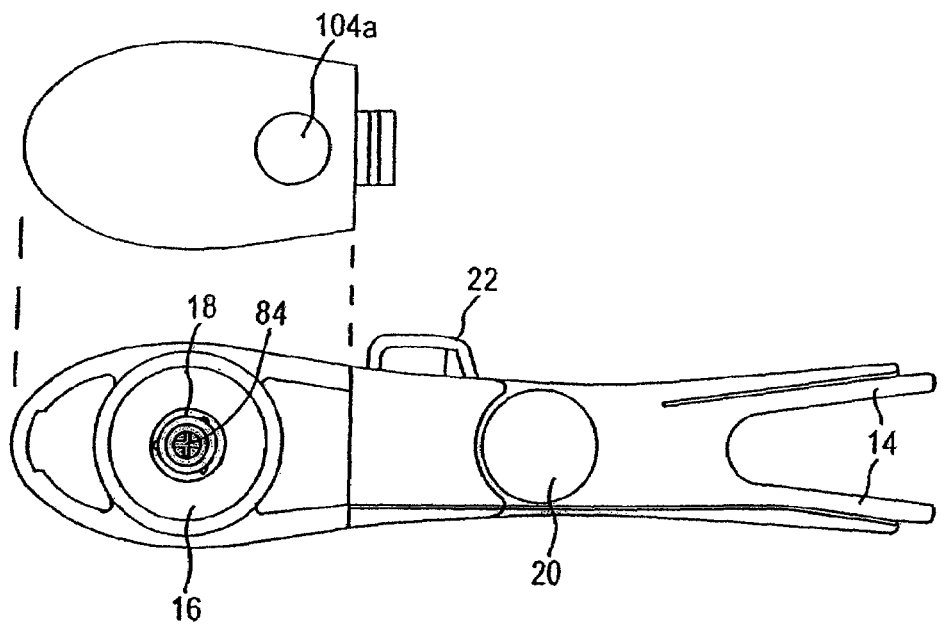
FIG. 5 is similar to FIG. 3 with the cover removed.

Mounting post 18 is placed over a boss 82 which extends upwardly from the bottom housing wall 48 and is secured thereto with a screw 84 as best depicted in FIG. 5. Mounting post 18 is free to rotate about a vertical axis of rotation 86 defined by boss 82. However, it will be appreciated that mounting post 18 is constantly prevented from free rotation as a result of constant engagement of the tensioning 'clicker' arm 32 with one of teeth 34. Furthermore, during periods of trigger deactivation, it will be appreciated that braking pawl 42 is in constant contact with another of teeth 34 with sufficient force exerted from spring 38 to prevent floss supply spool 16 from undesired rotation such as during flossing. It is only when trigger 22 is depressed that pawl 42 is free to pivot outwardly about post 40 into a disengaged position from mounting post 18 and thereby enable rotation of the take-up spool and the mounting post under tensional ratcheting bias produced by arms 28, 30 and 32 as aforesaid.

Figure 7:
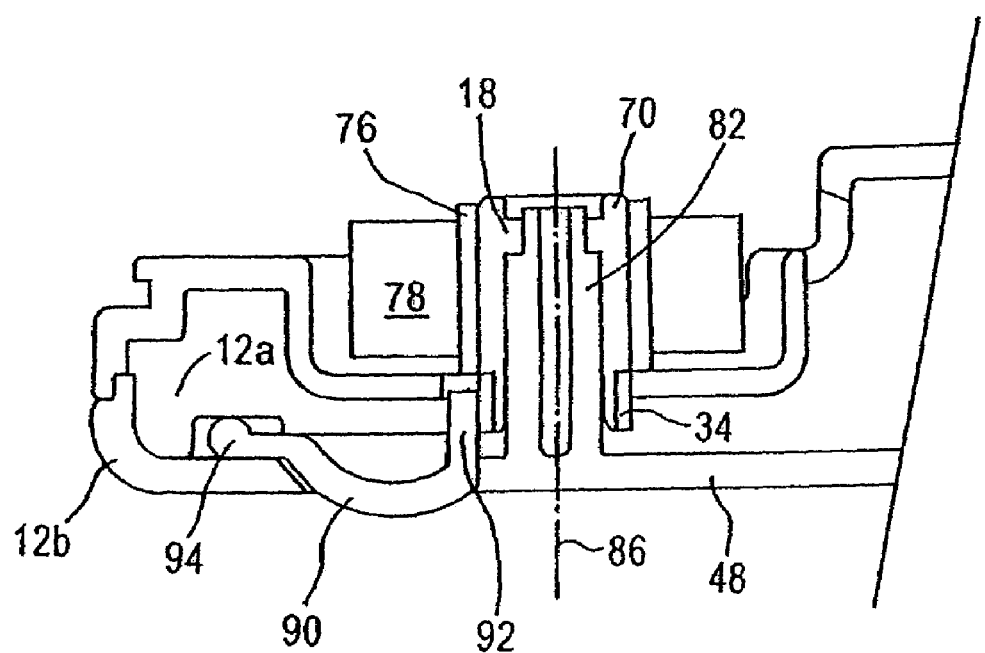
FIG. 7 is an enlarged sectional view of the supply spool.

Referring now to FIG. 7, it can be further seen that a depressible eject button 90 is formed in the bottom housing wall 48 that includes an ejection finger 92 located below and in vertical alignment with the floss supply spool or core 76. Therefore, when the eject button 90 is depressed upwardly, finger 92 is lifted in order to push on the bottom surface of the plastic core 76, causing the key grooves 74 to slide along key ribs 72 in the upward direction to release the supply spool from the post 18. The eject button 90 is resiliently biased to return to its lowermost deactivated position depicted in FIG. 8, at which time a fresh spool may be fitted to post 18 in the manner described above.

The manual dental flossing device 10 of the present invention possesses numerous advantages over prior art flossers of which we are aware. For example, locating the take-up spool 20 outside of the tension and ratcheting arrangements disposed within housing sections 12a, 12b, advantageously avoids contamination within the housing by used floss and results in easy cleaning with water to prevent the occurrence of an unhygienic situation. The keyed mounting of the supply spool 16 also outside the housing 12 advantageously allows an empty supply spool to be easily detached from its keyed shaft to facilitate rapid replacement with a fresh supply spool. The feature of providing plural keys preferably along the entire height of the floss supply spool is particularly advantageous to account for possible slippage of the spool on the mounting post, especially if large manufacturing tolerances are present between these component parts.

With the exception of the preferred use of a metallic floss cutter blade, return spring and screws, all components of the flosser 10 are preferably manufactured from plastic material. By providing plural keyways between the supply spool and post 18, larger manufacturing tolerances can be tolerated which allows for the possibility of lower manufacturing cost.

Further, the feature of providing a pair of offset ratchet pawls 26 and 28 advantageously assures a high degree of tension in the flossing circuit on the take-up side while brake pawl 42 in combination with tension arm 32 assures positive locking or braking engagement preventing unwinding on the supply side.

Eject button 90, as best depicted in FIG. 8, has an anchoring end 94 preferably trapped between the top and bottom housing portions 12a, 12b. Thus, installation of this eject button into the final product is easy.

Finally, a metal cutter 100 is preferably disposed in housings 12a, 12b to enable floss to be cut such as upon completion of flossing at which time the consumer will unwind the used floss from the take-up spool 20 and use the cutter on the bottom of the unit to cut the floss. The unit 10 is then preferably washed to maintain proper sanitation and the lead end of fresh floss can now be re-strung between the forks 14 and rewound several turns in the groove of the take-up spool 20. A slot 101 formed in the housing includes a bottom in which the cutter 100, is exposed. The slot is wide enough for floss to pass through but small to prevent a consumers finger from reaching the cutter blade.

Figure 4:
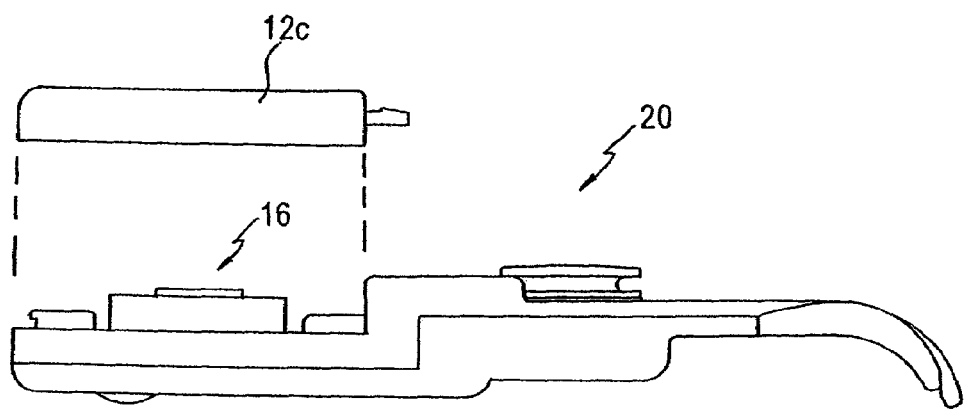
FIG. 4 is a view similar to FIG. 1 with the cover removed.

The body of the flosser 10 may also include a pair of deep grooves 102a that runs from the supply spool, to the ends of the forks 14 and ends up at the take-up spool. This is best depicted in FIG. 4. These deep grooves 102a function as a channel to guide the floss along the correct path, to keep the floss clean and away from the consumer's hand and to prevent the consumer from pressing on the floss while trying to advance it.

With the foregoing components, it will also be appreciated that tension can be imparted to the floss in the flossing circuit by applying thumb or finger pressure to the upper surface of take-up spool 20 to impart rotational movement to the take-up spool in the winding or counterclockwise direction. Depending on the degree of ratcheting force designed into pawls 32, 26 and 28, it may be possible for a predetermined amount of finger pressure against the upper surface of take-up spool 20 to override the ratchet mechanism to impart tension. In the alternative, tension may be continuously applied by maintaining manual rotational pressure or force against the upper surface of the take-up spool 20. Furthermore, depending on the degree of brake force that pawl 42 applies to teeth 34, it may also be possible to advance the floss in the circuit by applying manual finger pressure to the upper surface of take-up spool 20 to override the brake.

The cover 12c, with reference to FIG. 4, preferably includes a transparent window 104a that enables the consumer to see the supply spool and know when to replace it.

Figure 10:
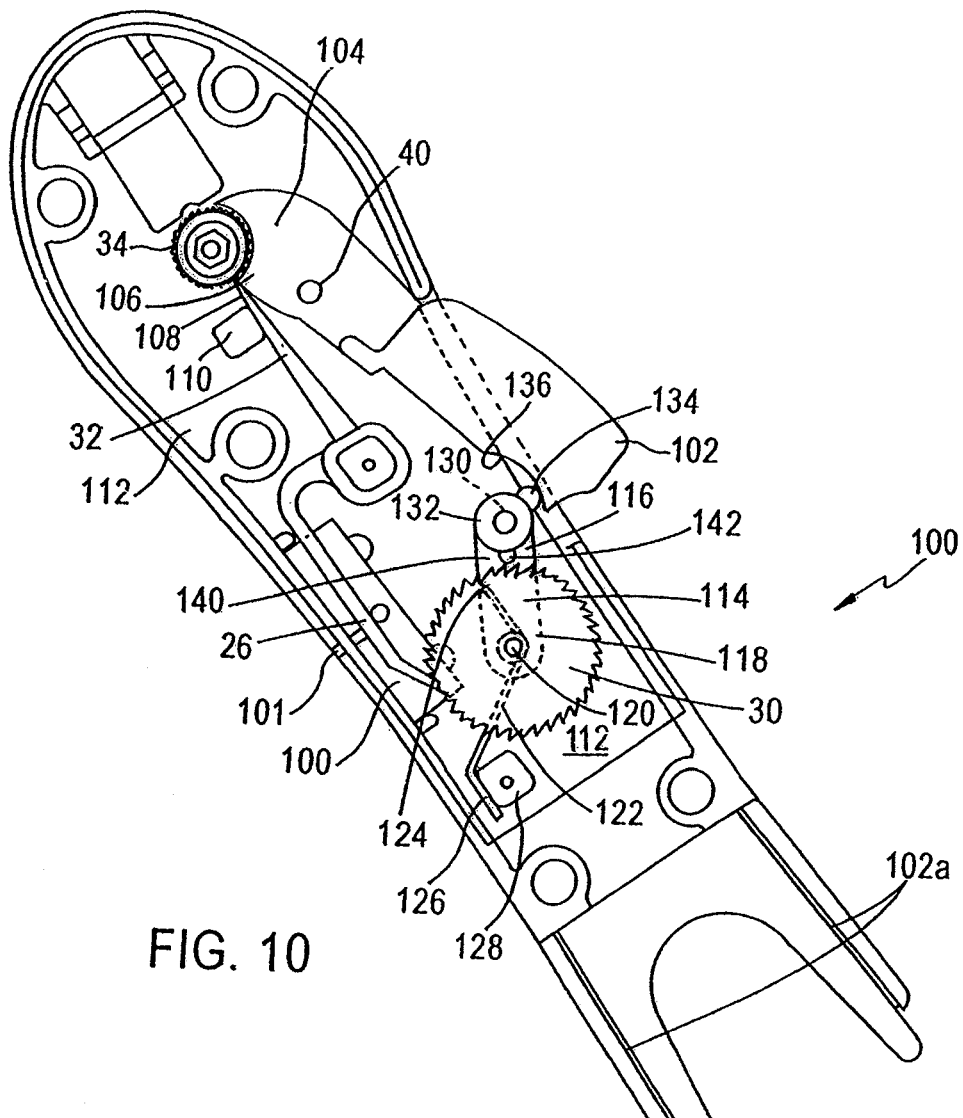
FIG. 10 is an enlarged top plan view with the top housing removed, to depict drive and tensioning mechanisms in connection with a preferred alternative embodiment of the flosser otherwise depicted in FIGS. 1 and 2.

FIG. 10 is an illustration of an alternate preferred embodiment of the invention which is almost identical to the previously described embodiments, with the following changes. When compared with FIG. 2, it can be seen that the improved flosser 100 of FIG. 10 includes a trigger 102 that is also pivotably mounted to the bottom housing 12b about a pivot post 40, but is formed without a brake tooth 42. Instead of brake tooth 42, the rearwardly extending portion 104 (i.e. extending rearwardly from post 40) includes an innermost braking or locking protrusion 106 adapted to abut against the free end 108 of clicker tension arm 32 immediately adjacent the point at which the clicker arm engages with the ratchet teeth 34 formed on the supply spool side of the flosser 100. With this arrangement, when trigger 40 is released to pivot outwardly from the housing under spring bias into the home position (FIG. 10), the spring biased braking portion 106 presses against the free end 108 of the clicker arm 32. Because of this, the clicker arm 32 is incapable of yielding movement and instead remains firmly locked between two of teeth 34 to prevent rotation of the supply spool 16 in the counterclockwise direction. A post or ridge 110 projecting upwardly from the interior bottom wall 112 of the bottom housing may be provided to prevent movement of the free end 108 of the clicker in a direction opposite the unwinding direction.

The feature of providing locking retention of the free end 108 of clicker tension arm 32 with locking or braking portion 106 assures that supply spool 16 cannot rotate in the unwinding direction after trigger 102 is released, thereby assuring tension in the floss supply circuit. In the FIG. 2 embodiment, experimentation revealed that tooth 42 would sometimes land on top of a supply spool ratchet tooth 34, instead of in the valley formed between two adjacent ratchet teeth. Consequently, tooth 42 would then often settle backward between two adjacent ratchet teeth 34, causing undesirable loosening of the floss supply circuit. This problem is effectively alleviated with the FIG. 10 arrangement.

Figure 11:
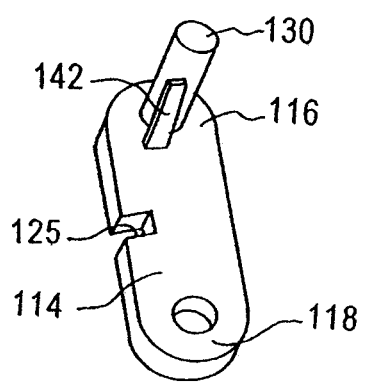
FIG. 11 is an enlarged perspective view of the ratchet arm of the FIG. 10 embodiment.

In the FIG. 2 embodiment, the strong compressive resistance of coil spring 38 during trigger actuation, in combination with the ratchet tension force applied by ratchet pawls 26 and 28 against ratchet 30, makes trigger depressment difficult for certain users, particularly for elderly persons, small children, and persons suffering from arthritis. To enable a reduced level of force needed to depress trigger 102, the FIG. 10 embodiment eliminates compression spring 38 and also provides a ratchet rotational arrangement that imparts greater torque with reduced manual force in order to turn ratchet 30. The arrangement features a ratchet arm 114 having one end 116 located in proximity to the forward end of the trigger 102 and an opposite end 118 extending forwardly and inwardly along the housing bottom wall 112 for pivotal attachment to a post 120 projecting upward from the bottom wall. A torsion spring 122 is wrapped around the ratchet arm mounting post 120 and has one end 124 engaging a notch 125 (FIG. 11) in an intermediate portion of the ratchet arm 114, and an opposite end 126 secured around an interior projection 128 so as to bias the ratchet arm end 116 in the clockwise direction. This biasing action normally disposes the distal end 116 of the ratchet arm 114 (i.e. closest to trigger 102) outwardly towards the trigger. This distal end 116 includes a post 130 projecting upwardly therefrom to which is mounted a cap 132 having a vertical rotational axis defined by the longitudinal axis of post 130. One side of the cap 132 is integrally formed with a ball-like cam follower projection 134 adapted to dwell in an arcuately shaped cam surface 136 formed in a forward and inwardmost portion of trigger 102. More or less diametrically opposed to this cam follower 134 on an inner side of cap 132 is a pawl 140 extending inwardly into meshing contact with the teeth of the large diameter ratchet 30. With this arrangement, depressing of trigger 102 causes the ratchet arm 114 to pivot counter-clockwise about its mounting post 120, against the bias of the torsion spring 122, which in turn causes the pawl 140 to turn with the ratchet arm about the mounting post 120, thereby imparting rotational movement to the ratchet wheel 30 and thereby take-up spool 20 in the winding direction. As the trigger is further depressed, it will be understood that cam follower 134 slides along cam surface 136. Pawl 140 is maintained in meshing driving contact with one of ratchet teeth 130.

When manual pressure is released from trigger 102, the torsion spring 122 resiliently displaces the ratchet arm 114 to its home position depicted in FIG. 10, in turn causing the trigger 102 to be returned to its disengaged position. During this returning movement, the pawl 140 is free to ride back over the ratchet teeth without encountering any significant resistance as a result of relative rotational movement of the cap 132 and thereby the pawl 140 about its mounting post 130. This relative movement can also be provided by providing a loose fit between the cap and post 130. Alternatively, instead of forming the pawl 140 and ratchet arm 114 as two separate components, it is possible to form these structures as a single component in which case the pawl should have sufficient natural flexibility to flex and ride over the ratchet teeth as the ratchet arm returns to the home position.

In comparison with the FIG. 2 embodiment, the ratchet arm construction 114 of FIG. 10 eliminates the need for small diameter driving ratchet 24. Further, by applying a trigger actuating force (i.e. through the cam surface 136 against the cam follower 134) at the distal end 116 of the ratchet arm 114 located furthest from the ratchet arm mounting post 120, it will be appreciated that the FIG. 10 construction takes advantage of a longer moment arm (i.e., greater leveraging or torque) than that afforded by the FIG. 2 construction to thereby advance the floss with less manual input force.

A tab 142 is fixedly secured to project upwardly from the upper surface of the ratchet arm 114 between the cap 132 and the intermediate portion of the ratchet arm. This tab 142 is primarily an aid in assembly of the pawl 140 on the ratchet arm since it properly locates the relative location of the pawl as the mounting cap is pushed downwardly onto the mounting post 130 during construction.

The foregoing ratcheting arrangement also enables the ratchet wheel 30 to be attached to the inside bottom surface of the top housing utilizing a screw that extends upwardly from the bottom surface of the ratchet wheel, through the thickness of the ratchet, upwardly through the top housing wall and into threaded engagement with the take-up spool 20. After the ratchet and take-up spool are screwed together through the top housing as aforesaid, the top housing may be secured to the bottom housing. When properly seated together, the ratchet wheel 30 is disposed co-elevationally adjacent the ratchet pawl 140 and the axis of rotation of the ratchet wheel is co-axial with the pivot axis of the ratchet arm 114. Since FIG. 10 is a view of the drive and tensioning mechanisms with the cover and top housing removed, it will be appreciated that the ratchet wheel 30 is shown in its relative location (as if the top and bottom housings were secured together) for ease of explanation only.

In the FIG. 10 embodiment, cutting blade 100 is positioned beneath pawl arm 26 for clamping contact against the housing bottom wall, thereby eliminating the need for a separate securement member as in the FIG. 2 embodiment.

It will be evident that there are additional embodiments which are not illustrated above but which are clearly within the scope in spirit of the present invention. The above description and drawings are therefore intended to be exemplary only in nature and the scope of the invention is to be limited solely by the appended claims.

The invention claimed is:

1. A flossing device, comprising:
   a housing including a fork extension extending from said housing and having a pair of prongs with grooves for guiding said floss in a circuit which spans a space between said prongs;
   a floss supply spool rotatably mounted to said housing;
   a floss take-up spool rotatably mounted to said housing;
   an actuating mechanism for rotating said take-up spool to advance floss within the floss circuit;
   a first tensioning mechanism connected to the floss take-up spool to tension the floss during periods when the actuating mechanism is deactivated, said first tensioning mechanism including at least one ratchet pawl engaging a ratchet co-rotatably mounted with the take-un spool; and
   a second tensioning mechanism connected to the sunply spool to cooperate with the first tensioning mechanism to tension the floss during periods when the actuating mechanism is deactivated;
   wherein the actuating mechanism further includes a brake engageable with the second tensioning mechanism to positively lock the supply spool by engaging the tensioning mechanism during periods when the actuating mechanism is deactivated.

2. The flossing device of claim 1, wherein said first tensioning mechanism includes a pair of said ratchet pawls engaging said ratchet.

3. The flossing device of claim 2, wherein said ratchet pawls are not part of said actuating mechanism.

4. The flossing device of claim 2, wherein
   said actuating mechanism comprises a pawi engageable with said ratchet to drive said ratchet, and hence said take-up spool, in a direction that causes unwinding of said supply spool when said actuating mechanism is activated, and
   said pawi of said actuating mechanism is different from said ratchet pawls of said first tensioning mechanism.

5. The flossing device of claim 1, wherein said second tensioning mechanism comprises
   circumferentially spaced teeth arranged on a lower portion of said supply spool; and
   a tension arm in co-elevational alignment with said teeth, projecting in a radial direction of said supply spool, and constantly engageable between a pair of said teeth.

6. The flossing device of claim 5, wherein said brake of the actuating mechanism is directly engageable with the tension arm of the second tensioning mechanism to positively lock the supply spool when the actuating mechanism is deactivated.

7. A flossing device, comprising:
   a housing including a fork extension extending from said housing and having a pair of prongs with grooves for guiding said floss in a circuit which spans a space between said prongs;
   a floss supply spool rotatably mounted to said housing;
   a floss take-up spool rotatably mounted to said housing;
   an actuating mechanism for rotating said take-up spool to advance floss within the floss circuit;
   a first tensioning mechanism connected to the floss take-un spool to tension the floss during periods when the actuating mechanism is deactivated, said first tensioning mechanism including at least one ratchet pnawl engaging a ratchet co-rotatably mounted with the take-up spool; and
   a second tensioning mechanism connected to the supply spool to cooperate with the first tensioning mechanism to tension the floss during periods when the actuating mechanism is deactivated;
   wherein said actuating mechanism includes
   a ratchet ann pivotally mounted to the housing,
   a pawl mounted to one end of said ratchet arm,
   a cam follower connected to the pawl, and
   a spring biasing the ratchet arm into a home position, said cam follower engaging a cam surface of a trigger in said actuating mechanism, whereby depressing of said trigger causes said pawl and said ratchet arm to pivot about the pivot axis of said ratchet ann, enabling the pawl to engage the ratchet and rotate the same and thereby the take-up spool.

8. A flossing device, comprising:
   a housing including a fork extension extending from said housing and having a pair of prongs with grooves for guiding said floss in a circuit which spans a space between said prongs;
   a floss supply spool rotatably mounted to said housing;
   a floss take-up spool rotatably mounted to said housing;
   an actuating mechanism for rotating said take-up spool to advance floss within the floss circuit;

a first tensioning mechanism connected to the floss take-up spool to tension the floss during periods when the actuating mechanism is deactivated; and a second tensioning mechanism connected to the supply spool to cooperate with the first tensioning mechanism to tension the floss during periods when the actuating mechanism is deactivated;

wherein said actuating mechanism comprises a trigger having opposite first and second ends and being rotatably mounted to said housing via a post located between said opposite ends;

when said trigger is deactivated, said first end brakes rotation of said supply spool; and when said trigger is activated, said first end releases said supply spool whereas said second end moves to drive said take-up spool to rotate in a direction that causes unwinding of said supply spool.

9. The flossing device of claim 8, wherein said second tensioning mechanism comprises circumferentially spaced teeth arranged on a lower portion of said supply spool; and a tension arm in co-elevational alignment with said teeth, projecting in a radial direction of said supply spool, and constantly engageable between a pair of said teeth.

10. The flossing device of claim 9, wherein said first end of the trigger of the actuating mechanism is directly engageable with the tension arm of the second tensioning mechanism to positively lock the supply spool when the actuating mechanism is deactivated.

11. The flossing device of claim 9, wherein said first end of the trigger of the actuating mechanism is directly engageable with the teeth on the lower portion of said supply spool to positively lock the supply spool when the actuating mechanism is deactivated.

12. The flossing device of claim 8, wherein said first tensioning mechanism includes a pair of said ratchet pawls engaging a ratchet co-rotatably mounted with the take-up spool, and wherein said ratchet pawls are not part of said actuating mechanism.

13. The flossing device of claim 8, wherein said first tensioning mechanism includes a pair of said ratchet pawls engaging a ratchet co-rotatably mounted with the take-up spool, the second end of said actuating mechanism comprises a pawl engageable with said ratchet to drive said ratchet, and hence said take-up spool, in a direction that causes unwinding of said supply spool when said actuating mechanism is activated, and said pawl of said actuating mechanism is different from said ratchet pawls of said first tensioning mechanism.

14. The flossing device of claim 8, wherein said actuating mechanism further includes a ratchet arm pivotally mounted to the housing, a pawl mounted to one end of said ratchet arm, a cam follower connected to the pawl, and a spring biasing the ratchet arm into a home position, said cam follower slidably engaging a cam surface at the second end of said trigger, whereby activation of said trigger causes said pawl and said ratchet arm to pivot about the pivot axis of said ratchet arm, enabling the pawl to engage a ratchet co-rotatably mounted with the take-up spool and rotate the ratchet, and hence the take-up spool, in the direction that causes unwinding of said supply spool.

15. The flossing device of claim 14, wherein said ratchet arm and said ratchet share the same pivot axis.

16. The flossing device of claim 14, wherein said cam follower and said pawl are integrated in a single body.

17. The flossing device of claim 14, wherein said ratchet arm, said cam follower and said pawl are integrated in a single body, said pawl being flexible.

18. The flossing device of claim 14, wherein said cam follower and said pawl are parts of a cap mounted rotatably on a post at said one end of said ratchet arm.

* * * * *